(12) United States Patent
Mahalingam et al.

(10) Patent No.: US 7,544,351 B2
(45) Date of Patent: Jun. 9, 2009

(54) TOPICAL LIGHTENING COMPOSITIONS AND METHODS OF USE

(75) Inventors: Harish Mahalingam, Ledgewood, NJ (US); Brian Jones, Warwick, NY (US); Gopinathan K. Menon, Wayne, NJ (US); Christos D. Kyrou, Goshen, NY (US); Michael Traudt, Brookfield, CT (US)

(73) Assignee: Avon Products, Inc, New York, NY (US)

(*) Notice: Subject to any disclaimer, the term of this patent is extended or adjusted under 35 U.S.C. 154(b) by 0 days.

(21) Appl. No.: 11/215,874

(22) Filed: Aug. 31, 2005

(65) Prior Publication Data

US 2005/0287089 A1 Dec. 29, 2005

(51) Int. Cl.
*A61Q 5/08* (2006.01)
*A61K 8/02* (2006.01)
*A61K 36/889* (2006.01)

(52) U.S. Cl. .......................... 424/62; 424/401; 424/727

(58) Field of Classification Search ........................ None
See application file for complete search history.

(56) References Cited

U.S. PATENT DOCUMENTS 7,014,844 B2 * 3/2006 Mahalingam et al.

FOREIGN PATENT DOCUMENTS

| JP | 2005-097654 | 4/1993 |
| JP | 06072838 A * | 3/1994 |
| JP | 2002-284663 | 10/2002 |

OTHER PUBLICATIONS

Cocos nucifera L.; Jul. 8, 1996 of the NewCROP website http://newcrop.hort.purdue.edu/newcrop/duke_energy/Cocos_nucifera.html, Center for New Crops & Plant Products at Purdue University.

* cited by examiner

*Primary Examiner*—Michele C. Flood
(74) *Attorney, Agent, or Firm*—Charles J. Zeller; Joan M. McGillycuddy; Anthony M. Santini

(57) ABSTRACT

There is provided a topical lightening composition having a melanin synthesis-regulating agent and a vehicle. Also, there is provided a topical lightening composition having an extract of perilla leaf and a vehicle. In addition there is provided a topical lightening composition having a lightening agent selected from the group consisting of coconut water, palm water, palm nut milk, pecan nut milk, almond nut milk, cashew nut milk, walnut nut milk, concentrates of the foregoing, and any combinations thereof, along with a vehicle. The compositions and methods of the invention are effective to lighten skin, hair, lips, and/or nails.

11 Claims, 1 Drawing Sheet

TOPICAL LIGHTENING COMPOSITIONS AND METHODS OF USE

BACKGROUND OF THE INVENTION

1. Field of the Invention

The present invention relates to the lightening of the skin, hair, nails and/or lips. The present invention further relates to compositions and methods for lightening the skin, hair, nails and/or lips.

2. Description of the Prior Art

Consumers, particularly those in Asia, have sought to lighten and reduce uneven pigmentation in the skin. Common skin conditions treated include freckles, age spots, dark spots, hyperpigmentation, discoloration, melasma, yellowing, and dark circles under the eyes.

Numerous substances have been applied to the skin to lighten the skin. Such substances include hydroquinone, kojic acid, licorice and/or its derivatives, ascorbic acid/ascorbic acid derivatives, arbutin, bearberry, *Glycyrrhiza glabra* and its derivatives, *Chlorella vulgaris* extract, perilla extract, and coconut fruit extract. Perilla extract is disclosed as a whitening agent in U.S. Pat. No. 5,980,904 and Japanese Publications 07025742, 07187989, 10265322, 2001163759, and 2001181173. Coconut fruit extract is disclosed as a whitening agent in Japanese Patent No. 2896815 B2. An extract of spongy mass of coconut tissue is employed in a tanning sunscreen composition in U.S. Pat. No. 5,756,099.

Skin and hair pigmentation is determined by the level of melanin present in the epidermis and hair fiber, respectively. Three different types of melanin are present in, for example, the epidermis: DHI-melanin, DHICA-melanin and pheomelanin. The different types of melanin vary in color or shade. DHI-melanin is the darkest and is blackish in color. DHICA-melanin is brownish in color. Pheomelanin is the lightest and is reddish in color.

Melanin is synthesized in specialized organelles called melanosomes within pigment-producing cells (melanocytes). Melanocytes respond to stimuli to regulate melanin synthesis.

Most conventional topical lightening agents act by interfering with the action of tyrosinase, the enzyme that catalyzes the conversion of the amino acid tyrosine to DOPAquinone. Previously, it has not been known that hypopigmenting could be achieved by inhibiting enzymes "downstream" from tyrosinase in the melanin synthesis pathway. It has now been discovered that the use of a melanin synthesis regulating agent that inhibits DOPAchrome tautomerase and/or DHICA-polymerase results in a composition with superior lightening, especially skin lightening.

It would be desirable to have a topical composition that provides enhanced levels of lightening, bleaching, hypopigmenting, whitening and/or depigmenting (hereinafter referred to individually and collectively as "lightening" or "lighten"). It would be further desirable to have a topical composition that contains lightening agents that acted to interfere with the conversion of DOPAchrome to DHI-melanin and DHICA-melanin. It would be yet further desirable to have a topical composition that contains lightening agents that act to inhibit or prevent the transfer (uptake) of melanin from the melanocytes to the keratinocytes. It would still yet be further desirable to have methods for lightening the skin, hair, nails and/or lips employing the compositions of the present invention.

SUMMARY OF THE INVENTION

It is an object of the present invention to provide a composition for lightening of the skin.

It is an object of the present invention to provide a composition to alter/modify melanin synthesis in the skin.

It is an object of the present invention to provide a composition to inhibit or prevent the uptake of melanin by keratinocytes.

It is an object of the present invention to provide methods for effecting the foregoing.

These and other objects and advantages of the present invention are provided by a topical lightening composition comprising a melanin synthesis-regulating agent, and a vehicle. There is also a topical lightening composition comprising an extract of perilla leaf and a vehicle. There is also a topical lightening composition comprising a lightening agent selected from the group consisting of coconut water, palm water, palm nut milk, pecan nut milk, almond nut milk, cashew nut milk, walnut nut milk, concentrates of the foregoing, and combinations of any of the foregoing, and a vehicle. There are also methods for lightening the skin, hair, lips, and/or nails comprising topically applying any one of these compositions.

DETAILED DESCRIPTION OF THE INVENTION

Figure 1:
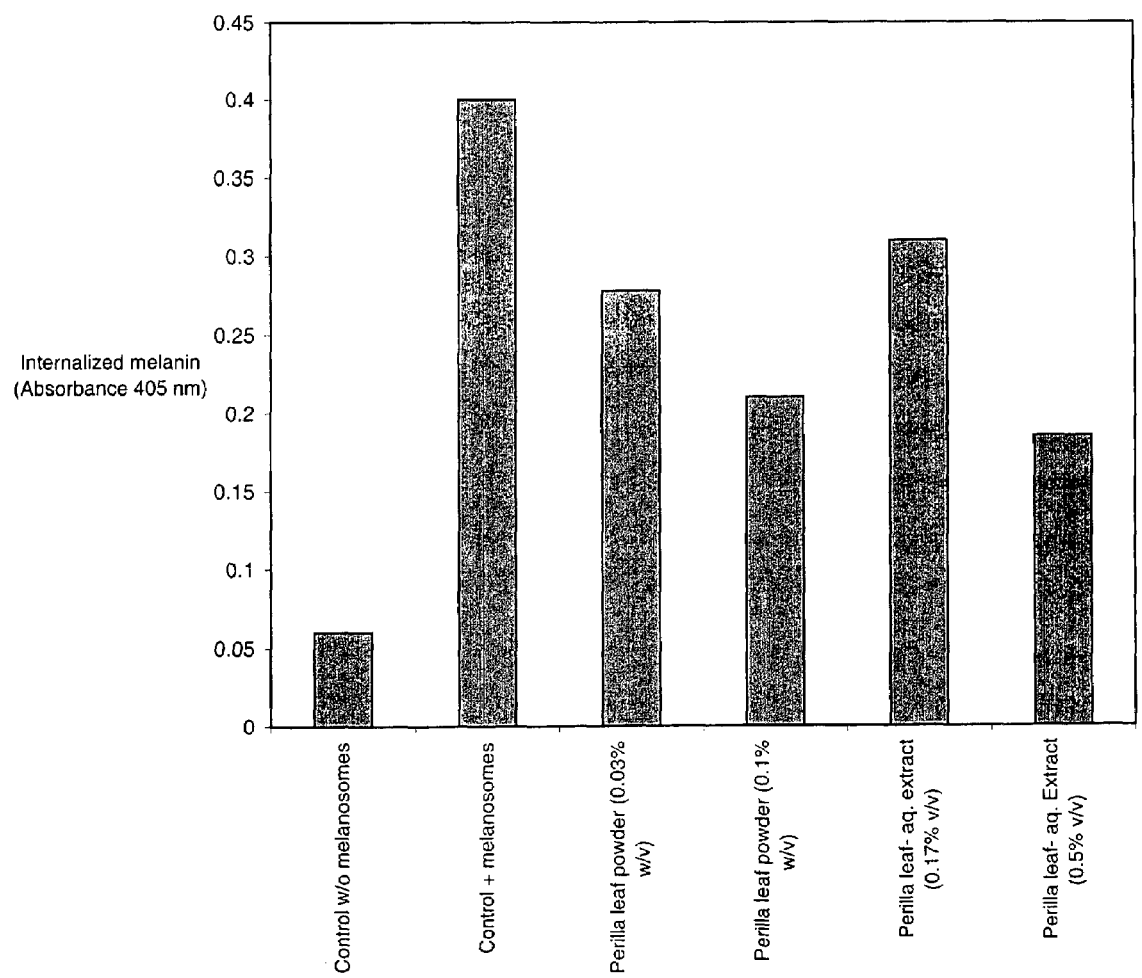
FIG. 1 illustrates the results of the melanin uptake assay in the Examples.

It was found surprising and unexpected that there were topical lightening compositions that provided enhanced levels of performance heretofore not possible. It was found possible to enhance lightening by inhibiting enzymes other than tyrosinase, specifically DOPAchrome tautomerase (DCT) and/or 5,6-dihydroxyindole-2-carboxylic acid polymerase (DHICA-polymerase). It was also found possible to enhance lightening by inhibiting and/or preventing the uptake of melanin by keratinocytes in, for example, the epidermis.

In its broadest aspects, the invention is not limited by any particular characterization of the physiological and/or chemical effects of topical lightening agents. However, the topical lightening agents useful in the compositions and methods of the present invention lighten the skin by regulating melanin production and inhibiting the uptake of melanin in the skin, hair, lips, and/or nails.

One embodiment of the present invention is the employment of a melanin synthesis-regulating agent individually, or in combination with a melanin uptake-inhibiting agent. When the melanin synthesis-regulating agent is present in an amount effective to inhibit DCT and/or DHICA polymerase, a superior lightening composition can be attained. It was heretofore unknown in the art that interference in this part of the melanin synthesis pathway could bring about lightening of the skin, hair, lips, and/or nails. A flow chart of the melanin synthesis pathway is as follows:

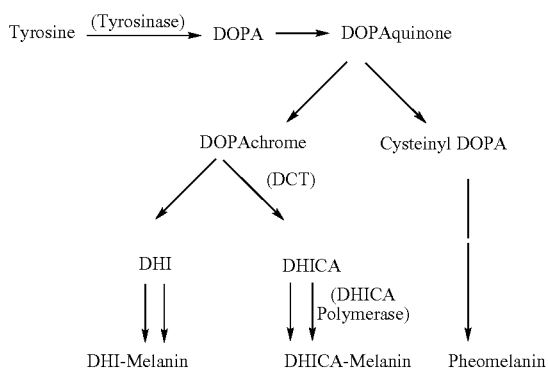

Moreover, the use of an additional agent that functions to inhibit the transfer (uptake) of melanin from the melanocytes to the keratinocytes further enhances the lightening efficacy of the present invention.

Examples of melanin synthesis-regulating agents include coconut water, coconut milk, palm water, palm nut milk, pecan nut milk, almond nut milk, cashew nut milk, walnut nut milk, concentrates of each of the foregoing, or combinations of any of the foregoing. Coconut water that has been concentrated, especially by freeze-drying, is most preferred.

Examples of melanin uptake-inhibiting agents include extracts or oils derived from all or parts of the perilla plant, e.g. the leaf, seed, stem, and root. A preferred agent is extract of the perilla leaf.

Another embodiment of the present invention is the use of perilla leaf extract as a lightening agent in a topical lightening composition, either individually or in combination with another lightening agent. Perilla leaf extract provides an unexpected enhancement of topical lightening efficacy compared to extracts, concentrates, or oils of other parts of the perilla plant, i.e. the seed, stem and root. In addition to enhanced efficacy, the perilla leaf extract can provide topical lightening efficacy at a lower amount compared to extracts of other parts of the perilla plant.

Another embodiment of the present invention is the use of any of the following as a topical lightening agent in a composition: coconut water, palm water, palm nut milk, pecan nut milk, almond nut milk, cashew nut milk, walnut nut milk, concentrates of the foregoing, or combinations of any of the foregoing. They can be used as the principal topical lightening agent or in combination with other lightening agents. Coconut water is preferred. A freeze-dried concentrate of coconut water is most preferred. Coconut water or the concentrate thereof is believed to provide superior lightening efficacy compared to extracts, concentrates, or oils of other parts of the coconut and/or coconut tree, i.e. the fruit, milk, shell, seed, leaf, and bark.

Topical lightening agents are present in the present composition at a level sufficient to induce the desired effect of lightening. The amount will vary depending upon the type of agent and the nature and level of desired effect. The lightening agent will typically be present from about 0.001 wt % to about 20 wt %, more preferably from about 0.01 wt % to about 5 wt %, and most preferably from about 0.1 wt % to about 2.5 wt %, based on the total weight of the composition.

The compositions of the present invention preferably include at least one, more preferably at least two, most preferably at least three, of the following ingredients: aloe barbadensis or an extract thereof, hydrolyzed soy protein, n-glucosamine, gamma-aminobutyric acid, a competitive inhibitor of melanocyte stimulating hormone (MSH) (e.g. hexapeptide-2), clintonia borealis (bluebeard lily) or an extract thereof, milk proteins, hydrolyzed milk proteins, sanguisorba officinalis (burnet), a glutathione reductase inhbitor (e.g. wheat germ) or extracts thereof.

The compositions of the present invention can be used to effectively lighten skin, hair, lips and nails be topically applying the composition having an effective amount of the topical lightening agent. To lighten the color or shade of hair, the present compositions should preferably be rubbed onto/into the scalp so that the composition can penetrate into the hair follicles or root shafts and be absorbed into the hair during the melanin production process.

The topical compositions of the present invention can be applied to treat a variety of skin conditions, including freckles, age spots, dark spots, hyperpigmentation, post-inflammatory hyperpigmentation, (e.g. post-acne hyperpigmentation), discoloration, melasma, yellowing, and dark circles under the eyes.

The present compositions may include any vehicle known in the art. Suitable vehicles include, but are not limited to, water; one or more vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones and polysiloxanes; hydrocarbon oils such as mineral oil, petrolatum, isoeicosane and polyisobutene; polyols such as propylene glycol, glycerin, butylene glycol, pentylene glycol and hexylene glycol; or combinations thereof.

Further optionally, the present compositions may include additional skin whitening agents known in the art. Examples of useful agents include the following: hydroquinone, kojic acid, licorice and/or its derivatives, ascorbic acid/ascorbic acid derivatives, arbutin, bearberry, *Glycyrrhiza glabra* and its derivatives, and *Chlorella vulgaris* extract. Other whitening agents are disclosed in U.S. Pat. No. 5,980,904, which is incorporated by reference herein.

Further optionally, the present compositions may include one or more of the following ingredients: anesthetics, antiallergenics, antifungals, antimicrobials, anti-inflammatories, antiseptics, chelating agents, colorants, emollients, exfollients, film formers, fragrances, humectants, insect repellents, lubricants, moisturizers, pharmaceutical agents, preservatives, skin protectants, skin penetration enhancers, stabilizers, surfactants, thickeners, viscosity modifiers, or vitamins.

The compositions can be made into any suitable product form. Such product forms include, but are not limited to, a cream, lotion, ointment, gel, foam, pomade, aerosol spray, pump spray, a stick, towelette, or patch.

EXAMPLES

The effect of coconut water (freeze-dried concentrate) on the melanin synthesis pathway was demonstrated with various assays using mouse melanoma cells from the S91 cell line (hereinafter "cells"). The cells were cultured in 1:1 mixture of Ham F10+10% horse serum and DMEM+10% fetal bovine serum. All cell experiments were conducted in a humidified, 5% CO2 incubator at 37 degrees C. Cells were treated with 0.02% and 0.05% w/v concentrations of coconut water (freeze-dried concentrate) respectively for 24 hours. Cell extracts were attained at 24 hours, and the following assays were performed: DOPAchrome Tautomerase (Example 1) and DHICA Polymerase (Example 2).

Example 1

DOPAchrome Tautomerase Assay (Coconut Water)

DOPAchrome Tautomerase (DCT) activity was assayed according to the method disclosed in Chakraborty et al., 1998, Effect of arbutin on melanogenic proteins in human melanocytes, Pigment Cell Res. 11: 206-212. Specifically, ice-cold DOPA (0.5 mg per ml of 0.1 M sodium phosphate buffer, pH 6.8) was mixed with $Ag_2O$ (30 mg $Ag_2O$: 1 mg DOPA) for about 1 minute and filtered through a 0.22 μm Millipore filter. DCT was assayed spectrophotometrically by adding up to 0.1 ml cell extract to 0.5 ml of a solution of freshly prepared DOPAchrome (~0.5 mg/ml). Reactions were carried out at room temperature in plastic cuvettes, and the disappearance of absorption at 475 nm was followed. Phenylthiourea (1 mM) was added to the reaction mixture, because the presence of tyrosinase in the cell extract can interfere with the assay. The percentage conversion of DOPAchrome was calculated per mg of protein extract and normalized against the control. It was demonstrated that 0.02% wt./vol. coconut water (freeze-dried) provided an average decrease in DOPAchrome conversion of 50% (42/58) as compared to the control.

Example 2

DHICA Polymerase Assay (Coconut Water)

A DHICA polymerase assay was done according to the method disclosed in Chakraborty et al., 1996, Polymerization of 5,6-dihydroxyindole-2-Carboxylic acid to melanin by the pmel17/silver locus protein, Eur. J. Biochem. 236: 180-188. Specifically, the cell extract (0.5 ml, 150-200 μg protein) was passed through a wheat germ agglutinin column (1 ml bed volume) equilibrated with lysis buffer. The bound material was eluted with 0.5 ml 1M N-acetyl glucosamine, which contains crude DHICA polymerization factor and other melanogenic proteins. A reaction mixture of 0.5 ml containing either the enzyme preparation to be measured (20 μg protein from wheat germ agglutinin eluates) or the appropriate buffer blank, DHICA (0.5 mM), and 100 mM sodium phosphate buffer, pH 7.0. Phenylthiourea was also included to inhibit endogenous tyrosinase activity in the preparation.

Spectrophotomeric reading of the absorbance of the reaction mixture was taken at T=0 and T=4 hours time points at 400 nm. DHICA-melanin, but not DHICA itself, has been shown to absorb light at these wavelengths (Orlow et al., 1992, Synthesis and characterization of melanins from dihydroxyindole-2-carboxylic acid and dihydroxyndole, Pigment Cell Res. 5: 113-121). An increase in absorbance over that seen in blank tubes was defined as specific DHICA polymerization factor activity. It was demonstrated that 0.02% wt./vol. coconut water (freeze-dried) provided an average of 52.5% (55%/50%) decrease in DOPAchrome conversion as compared to the control. At 0.05% wt./vol. coconut water (freeze-dried) provided an average decrease of 75% (74/76) in DOPAchrome conversion as compared to the control.

Example 3

Melanosome Uptake Assay (Perilla Leaf Extract)

Melanosome Isolation

Confluent cultures of B16 melanocytes produce moderate levels of melanosomes. However, to induce elevated melanosome production in this cell line, semi-confluent (60%) cultures of B16 cells were treated for approximately 36 hours with normal growth medium supplemented with 10 mM ammonium chloride (final conc.). The medium was then aspirated and the hypermelanotic cells were washed (2×2 ml) with distilled water to provide a hypotonic stress to the cells. An aliquot (2 ml) of a hypotonic lysis solution (0.02% NP-40 in water) was added to each plate and the plates were incubated for approximately 5 min at room temperature. Following verification of cell lysis using light microscopy, the cellular material from three (3) culture plates were pooled in a 15 ml conical tube and centrifuged at approximately (200×g) for 5 minutes to remove cellular debris. The resulting supernatant containing melanosomes was transferred to a clean 15 ml conical tube and centrifuged (850×g) for 20 minutes. The resulting pellet containing the isolated melanosomes were resuspended in 1 ml of Phosphate Buffered Saline (PBS) and stored at 4° C. until used.

Treatment of Keratinocytes with Melanosomes

The normal human epidermal keratinocytes (NHEKs) (available from Clonetics, Inc.) were plated in the wells of 24-well plates at a density of 200,000 cells/well. Approximately 24 hours later, the growth medium was replaced with 1 ml of the appropriate growth medium (i.e., DMEM/KGM-2) containing the melanosome preparation with or without additional treatment conditions. The cells were treated with different concentrations of perilla leaf extract (powder form or aqueous form). The cells were then returned to the incubator for approximately 1.5 hours. For these studies, each well of keratinocytes was treated with the amount of melanosomes isolated from a single plate of B16 cells.

In some experiments, the 24 well plates of treated keratinocytes were centrifuged for 15 minutes at 1,000 rpm to facilitate the deposition of the melanosomes onto the surface membranes of the keratinocytes. The plates were then returned to the incubator for 1.25 hours.

Analysis of Melanosome Uptake

For analysis, the cells in each well of keratinocytes were rinsed (3×1 ml) with PBS, removed from the plate using trypsin/EDTA, washed with PBS. To analyze the uptake of melanosomes by the keratinocytes, the internalized melanin was extracted from the cells according to a modified method of Bessou-Touya, S., et al. (Chimeric human epidermal reconstructs to study the role of melanocytes and keratinocytes in pigmentation and photoprotection. J. Invest. Dermatol., 111:1103-1108, 1998) and quantified spectrophotometrically by determining the melanin-specific absorbance at 405 nm.

Results

Melanocytes synthesize melanin and deposits onto melanosomes. Visual manifestation of skin color is due to presence of melanin/melanosomes in keratinocytes. Melanosomes are taken up by keratinocytes and the rate of uptake, retention and processing of melanosomes in the keratinocytes is a key determinant of skin color. Thus, the internalized melanin value reflects the amount of melanin/melanosome uptake and retention by the keratinocytes. Thus, lower internalized melanin values, particularly internalized melanin values that are less than the control with melanin, indicate that melanin uptake by the keratinocytes has been inhibited. As illustrated in FIG. 1, internalized melanin values for perilla leaf extract were lower than internalized melanin values of the control with melanin.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of lightening skin, hair, lips, and/or nails, comprising: applying topically to an area of the skin, scalp, hair, lips, and/or nails in need of lightening a composition having a topical lightening agent and a vehicle, wherein the topical lightening agent has a melanin synthesis-regulating agent of coconut (*cocos mucifera*) water, wherein the melanin synthesis-regulating agent is present in an amount effective to inhibit DOPAchrome tautomerase, 5,6-dihydroxyindole-2-carboxylic acid polymerase, or both, and is present in an amount of about 0.001 to about 20 weight percent based on the total weight of the composition.

2. The method of claim 1, wherein the topical lightening agent is a freeze-dried concentrate of coconut water.

3. The method of claim 1, wherein the topical lightening agent is present in an amount of about 0.01 to about 20 weight percent based on the total weight of the composition.

4. The method of claim 1, wherein the topical lightening agent is present in an amount of about 0.01 to about 5 weight percent based on the total weight of the composition.

5. The method of claim 1, wherein the topical lightening agent is present in an amount of about 0.1 to about 2.5 weight percent based on the total weight of the composition.

6. The method of claim 1, wherein the topical lightening agent is topically applied to the skin.

7. The method of claim 6, wherein the composition is topically applied to treat a skin condition selected from the group consisting of freckles, age spots, dark spots, hyperpigmentation, post-inflammatory hyperpigmentation, discoloration, melasma, yellowing, dark circles under the eyes, and any combinations thereof.

8. The method according to claim 1, wherein the composition is in a product form selected from the group consisting of a cream, a lotion, an ointment, a gel, a foam, a pomade, an aerosol spray, a pump spray, a stick, a towelette, and a patch.

9. The method of claim 1, wherein the vehicle is selected from the group consisting of vegetable oils, esters, alcohols, fatty alcohols, isoparaffins, silicone oils, polyols, and mixtures thereof.

10. The method of claim 2, wherein the topical lightening agent is present in an amount of about 0.1 to about 2.5 weight percent based on the total weight of the composition, and wherein the composition is topically applied to treat a skin condition selected from the group consisting of freckles, age spots, dark spots, hyperpigmentation, post-inflammatory hyperpigmentation, discoloration, melasma, yellowing, dark circles under the eyes, and any combinations thereof.

11. The method of claim 6, wherein the topical lightening agent is a freeze-dried concentrate of coconut water, and wherein the topical lightening agent is present in an amount from about 0.001 to of about 20 weight percent based on the total weight of the composition.

* * * * *